United States Patent
Tokita et al.

(10) Patent No.: US 6,500,109 B2
(45) Date of Patent: Dec. 31, 2002

(54) PROSTATE TREATMENT TEMPLATE

(75) Inventors: Ken Tokita, Los Angeles, CA (US); Bibianna Ahrum Cha, St. Louis, MO (US); James Bryan Prichard, St. Charles, MO (US)

(73) Assignee: Tayman Medical, Inc., Chesterfield, MO (US)

( * ) Notice: Subject to any disclaimer, the term of this patent is extended or adjusted under 35 U.S.C. 154(b) by 0 days.

(21) Appl. No.: 09/910,118

(22) Filed: Jul. 19, 2001

(65) Prior Publication Data

US 2002/0038117 A1 Mar. 28, 2002

Related U.S. Application Data

(60) Provisional application No. 60/219,866, filed on Jul. 21, 2000.

(51) Int. Cl.⁷ .............................. A61N 5/00; A61M 5/00
(52) U.S. Cl. ........................................... 600/7; 604/116
(58) Field of Search ........................... 600/1–7, 8, 459, 600/461–464, 444, 449; 424/1.11; 604/116; 606/130, 71, 108

(56) References Cited

U.S. PATENT DOCUMENTS 5,868,757 A * 2/1999 Koutrouvelis .............. 424/1.11
5,871,448 A * 2/1999 Ellard ........................ 600/459
5,931,786 A * 8/1999 Whitmore et al. .......... 600/459
5,961,527 A * 10/1999 Whitmore et al. .......... 606/130
6,036,632 A * 3/2000 Whitmore et al. .............. 600/7

FOREIGN PATENT DOCUMENTS

WO WO 0187164 A2 * 11/2001 ........... A61B/17/00

* cited by examiner

Primary Examiner—Eric F. Winakur
Assistant Examiner—Nikita R Veniaminov
(74) Attorney, Agent, or Firm—Paul M. Denk

(57) ABSTRACT

A disposable prostrate treatment template and a separate mounting frame to mount the template to a seed implant device is provided. The template includes a template body having a plurality of apertures extending therethrough; fasteners for removably securing said template to said mounting frame; suture wings extending from said template body to facilitate suturing of said template to a patient; and belt loops sized to receive a belt to secure the template to a patient. The template body is made from a rigid body frame and a polymer portion molded to said body frame. The body frame includes at least a pair of spaced apart legs and a cross-member extending between and connecting the legs to define a center area of the body in which the apertures are positioned. The apertures include at least one detent in the aperture and a flared entrance to the aperture. To align the template on the frame, the frame includes pins, and the template includes holes (preferably in the body frame) through which the pins extend.

12 Claims, 5 Drawing Sheets

PROSTATE TREATMENT TEMPLATE

CROSS-REFERENCE TO RELATED APPLICATIONS

This application claims priority to Provisional Application Ser. No. 60/219,866 filed Jul. 21, 2000, entitled "Prostate Treatment Template", and which is incorporated herein by reference.

STATEMENT REGARDING FEDERALLY SPONSORED RESEARCH OR DEVELOPMENT

Not Applicable.

BACKGROUND OF THE INVENTION

This invention relates in general to prostate implanting devices, and more specifically to a disposable guide that can be used alone or in conjunction with other seed stabilization devices, for treatment of prostate cancer.

Prostate cancer is the most common malignancy of the male genitourinary tract. In 1998, the number of cases of prostate cancer in the United States, alone, was estimated to be 184,500, with approximately 39,200 men dying of the disease annually. (Landis, S. H., Murray T., Bolden, S., et al: *Cancer Statistics* 1998. *CA Cancem J. Clin* 48:6–29, 1998).

The various methods for treatment include surgical intervention, external radiotherapy, brachytherapy seed implants, high dose rate brachytherapy, cryotherapy (freezing) and RF (heat) therapy.

Surgical intervention and external radiotherapy are widely known. The latter treatment method involves two basic steps:

1. Guide interventional device(s) into the prostate gland under ultrasound guidance, either with or without a stabilizing device.
2. Kill tissue by delivering energy, or in the case of cryotherapy, by taking away energy.

Brachytherapy is defined as the use of permanent implants or radioactive materials at the site. Brachytherapy has been successfully used in the treatment of prostate cancer. This is especially true when performed with the aid of implant stabilization devices, such as the AccuSeed, designed and manufactured by Tayman Medical, Inc., located in Chesterfield, Mo. The Tayman Medical AccuSeed stabilization device cradles the ultrasound probe so that the prostate gland can be viewed in real-time while inserting interventional devices through bores in the template to facilitate therapy. The bores in the template simply guide needles, etc. through the perineum and into the prostate gland.

High Dose Rate Brachytherapy involves temporary insertion of radioactive wires. The term radiation refers to energy propagated through space to destroy tissue. Cryotherapy is defined as the use of a very low temperature instrument to freeze tissue. RF therapy is defined as the use of electric current to heat tissue via an instrument that is in contact with the tissue.

Disadvantages associated with surgical intervention include impotence and incontinence due to damage of tissues in close proximity to the prostate, such as seminal vesicles and essential nerve bundles. External radiation can also have deleterious effects on surrounding normal tissues (e.g., seminal vesicles, essential nerve bundles, bladder, rectum, and the urethra). With permanent brachytherapy seed implants there is a potential for radiation exposure to hospital staff and family members because the radioactive seeds leave the facility with the patient. High dose brachytherapy has the disadvantage that it also involves radioactivity, although no radioactive materials leave with the patient. Researchers in cryotherapy and RF therapy are challenged to accurately predict heat transfer in the very complex system comprised of the prostate and surrounding tissues.

Advantages of high dose rate brachytherapy include higher confidence in dose calculations because treatment planning is done using actual needle positions after needle placement. This technique can reduce exposure to surrounding tissues such as the bladder and rectum. The short treatment time adds to the patient's comfort, and no residual radioactive materials or tissue remain in the patient when the procedure is over. Some of the above advantages, as well as the procedures and techniques, are pointed out in Rodriguez, et al, *High Dose Rate Brachytherapy In Treatment Of Prostate Cancer* 13(3) pp. 503–523, 1999, *HematologylOncology Clinics of North America*.

Brachytherapy is defined as the use of permanent implants or radioactive materials at the site. Two forms of brachytherapy for the treatment of prostate cancer are seed implantation and high dose rate brachytherapy:

Seed Implantation is performed on an out-patient basis under spinal anesthesia. The transrectal ultrasound probe is re-positioned to accurately reproduce the conformational plan format. Disposable implant needles that have been preloaded with radioactive seeds and absorbable spacers are then introduced through the appropriate needle guide holes in a template as indicated in the plan. Each needle is guided through the perineum to its predetermined position within the prostate under direct ultrasound visualization of the needle position within the prostate. The specified number of seeds are then implanted by withdrawing the needle while holding the stylet against the stylet stop. The seeds are pushed out as the needle is withdrawn by the stationary stylet. The AccuSeed Stepper, from Endocare, Irving, Calif., is used to position and stabilize the ultrasound probe and the implant needles.

The high dose radiation procedure is performed in the operating room using a spinal or general anesthesia. The patient is positioned in lithotomy position. The AccuSeed stepper is setup, and a high dose radiation template is mounted to the base and set up adjacent to the perineal area of the patient. The TRUS is utilized for the identification of the prostate gland. With the use of TRUS and fluoroscopic guidance, the implant needles are carefully inserted through the skin surface to the prostate gland. X-rays verify needle position. The template is then sutured at all four corners to the perineum. The catheters remain in place as the AccuSeed stepper is taken down and away from the patient. X-rays are utilized to optimize a specific treatment plan. When the dose is finalized the HDR remote afterloader is programmed with your individual treatment. The patient is then taken to the radiation oncology department. The implant catheters are connected to an HDR machine, to enable a radiation source to deliver treatment. The number of HDR treatments depends on the individual's prescription.

Cryotherapy is defined as the application of extreme cold to destroy tissue.

The cryotherapy procedure is performed with a local or spinal anesthesia. The patient is placed in lithotomy position and prepped and draped. The AccuSeed is set up and the cryotherapy template is mounted on the stepper to assist in holding the TRUS and placement of the cryotherapy probes. The prostate gland is measured with TRUS and the plan is evaluated for placement of the cryotherapy probes. The guide wires and dilators are then inserted under ultrasound at planned locations. A urethral warmer and thermocouples are placed in delineated areas to measure and protect surrounding tissues. A first freeze is accomplished with liquified argon gas. This gas creates ice balls as the tip of the cryoprobes encompassing the entire prostate gland. Extreme cold temperatures destroy all the prostate tissue including cancerous cells. After a thawing period of about thirty minutes, a second freeze is done to ensure effective treatment has been accomplished.

The most prevalent use of the current invention will be in high dose rate brachytherapy due to the need for the template to remain attached to the patient for extended periods, and that the treatment methods inherently include safety, efficacy, and popularity of its usage due to elimination of the inconvenience that occurs in the standard type of treatments as explained above.

SUMMARY OF THE INVENTION

This invention principally relates to a prostate implanting device, and more specifically provides for the very accurate seeding of a prostate malignancy at the exact site of its determined location, through the usage of the treatment template of this invention.

The present invention is a disposable template (also called a guide or a grid) to be used either freehand or in conjunction with the AccuSeed™ Stepper and Stabilizer, currently available from Tayman Medical, Inc., of Chesterfield, Mo. Although designed for use with the AccuSeed stepper and stabilizer, the template could be modified for use with other stepper/stabilizers.

The template of this invention provides a guiding and anchoring means for interventional devices associated with brachytherapy seed implants, high dose rate brachytherapy, cyrotherapy, and RF therapy, such as needles and catheters. This template may be used free hand, in conjunction with the treatment of a patient suffering from prostate cancer.

This prostate treatment template is generally used in conjunction with a medical seeding device, as the type as previously identified, and is designed to be attached to the seeding device, and registered relative thereto, such that when assembled, the calibration tank or stabilization device accurately mates the entire assembly together, to make it highly accurate in the seeding of an implant at a precise location within the prostate, during treatment.

As shown in the drawings, the template and the interface optionally contain a sensing means (such as a proximity sensor, by way of example only) that detects templates and may prevent future electronic/motorized stepper/stabilizers from operating in the presence of counterfeit templates.

The interface facilitates docking and undocking of the template in a convenient way that is consistent with clinical procedures. For instance, during high dose brachytherapy procedures, the interface allows the stepper/stabilizer to undock from the template, leaving the template behind with the patient without disturbing the interventional devices that have been inserted. Further, the interface is of an open design, which would allow it to be removed even if those interventional devices are connected to external equipment, such as a high dose brachytherapy afterloader. The interface also uniquely allows the template to be reconnected to the stepper/stabilizer regardless of what interventional devices are connected to the template, and for whatever reason.

It is, therefore, the principal object of this invention to provide for the combination of a template, for support within its interface holder, to furnish very accurate seeding of high dose rate means for brachytherapy treatment, etc., of malignancy within the prostate.

Another object of this invention is to provide for a template which when located within its holder is precisely in registration with the seeding instrument with which it is used.

Another object of this invention is to provide for a treatment template that has various other accessories that add to the convenience of usage of the device, when used for implanting a seed for treatment of prostate cancer.

These and other objects may become more apparent to those skilled in the art upon reviewing the summary of the invention as provided herein, and upon undertaking a study of the description of its preferred embodiment, in view of the drawings.

Some of the are unique features of the new product include:

1. A disposable or reusable polymer template insert molded to a metal frame, with portions of either exposed, and portions of either encapsulated in the other.
2. A frame that facilitates registration/calibration and adds physical strength.
3. A template with belt loops to accommodate a support belt.
4. A template with suture wings for support during the extended time the template remains with the patient.
5. A template with finger grip areas for hand manipulation.
6. A template with finger grip areas that double as clearance for monitoring components during calibration or when not used in an handheld mode.
7. A template with unique instrument alignment bores composed of a hole for directional guidance and one or more detents to control device insertion/removal force.
8. A template and template interface that mate together and with the Tayman Stepper/Stabilizer, according to a proprietary design.
9. An interface that registers the template to the stepper/stabilizer, guaranteeing calibration without re-calibration for each template used.
10. An interface that is of an open design.

DESCRIPTION OF THE PREFERRED EMBODIMENT

Figure 1A:
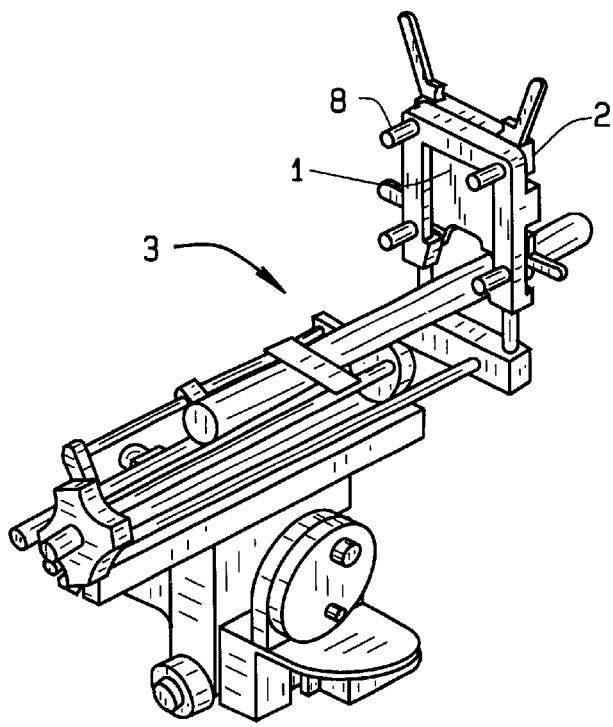
FIG. 1a is an isometric view of the disposable template connected to a mounting frame and mounted on a seeding instrument.
Figure 1B:
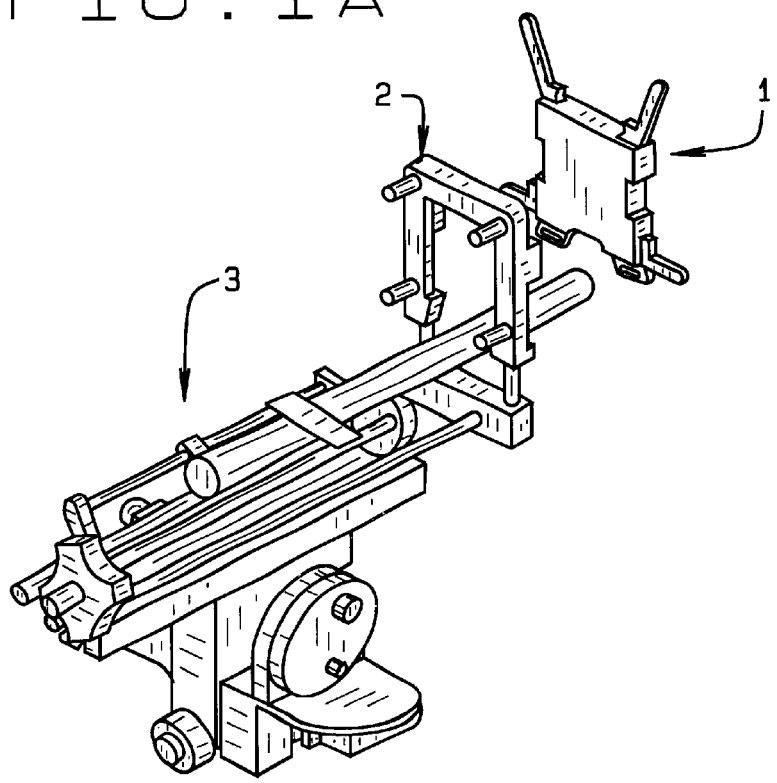
FIG. 1b discloses the disposable template displaced from its mounting frame.

In referring to the drawings, and in particular FIGS. 1a and 1b, the disposable template 1 is shown in two of its positions. FIG. 1a shows the template connected with its mounting frame 2; and with the template and mounting frame are secured to the seed implanting device 3 (i.e., a stepper/stabilizer) as previously explained, in preparation for the seeding of a malignancy within a prostate, during treatment. FIG. 1b shows the mounting frame 2 mounted to the stepper/stabilizer 3, and with the template 1 positioned to be mounted to the frame 2. The frame 2 is very accurately set with respect to the seeding device 3, such that when the disposable template 1 is arranged therewith, it is highly accurate in its setting with respect to providing very precise positioning and insertion of the needle holding the radiation seed, as it is implanted into the prostate, at a precise location where the cancer has been detected.

The template 1 and its interface optionally contain a sensing means (such as a proximity sensor, by way of example only) that detects when the proper template is being used, and prevents any future electronic/motorized stepper/stabilizer from operating in the presence of any counterfeit template. The interface or mounting frame 2 facilitates docking and undocking of the template in a convenient way that is consistent with clinical procedures. For example, during high dose brachytherapy procedures, the interface allows the stepper/stabilizer 3 to undock from the template 1, leaving the template behind with the patient without disturbing the interventional devices that have been inserted. Further, the interfaces of an open design, which would allow it to be removed even if those interventional devices are connected to external equipment, such as high dose brachytherapy afterloader. The interface also uniquely allows the template 1 to be reconnected to the stepper/stabilizer 3, regardless of what interventional devices are connected to the template, and for whatever reason.

Figure 2:
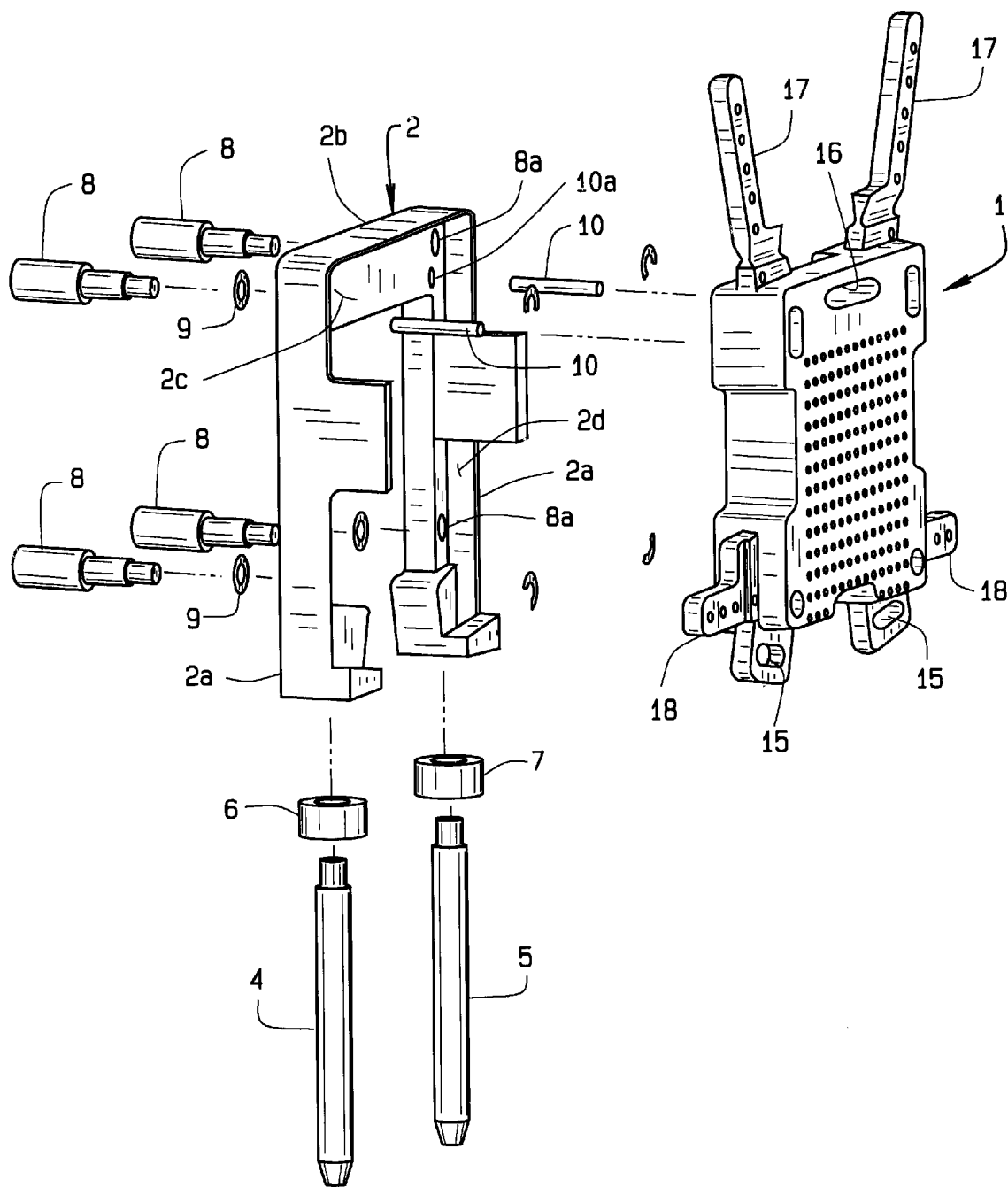
FIG. 2 is an exploded view of the treatment template of this invention, its mounting frame, and the means for securing it with the seeding instrument.

FIG. 2 provides an exploded view of the disposable template 1, and its frame 2. The frame 2 is designed for holding the template 1 in place, once assembled, to provide a very accurate gauge for positioning of the seeding needle (s), for use for providing precision to the locating of any treatment seed, within the cancerous location of the prostate. There are provided vertical grid posts 4 and 5, that mount to the bottom of the frame, through the sleeves 6 and 7, while the posts themselves are usually provided upon the seeding device 3, as previously explained. The frame 2 is of an inverted U-shape configuration, having a pair of legs 2a and a top or cross-member 2b. The legs 2a and cross-member 2b are generally L-shaped in horizontal cross-section, defining a back 2c and walls 2d. The legs 2a and cross-member 2b are sized so that the back 2c and walls 2d cradle the treatment template 1 to facilitate positioning of the template with respect to the mounting frame 2. The mounting frame 2 includes a series of apertures 8a in the back 2c in alignment with thumb screws 8, that extend through washers 9, for threadedly engaging the template 1, in place, when installed. The guide pins 10 further facilitate the precision alignment of the template 1 and frame 2, when assembled. The guide pins 10 are received in holes 10a in the frame back 1c.

Figure 3:
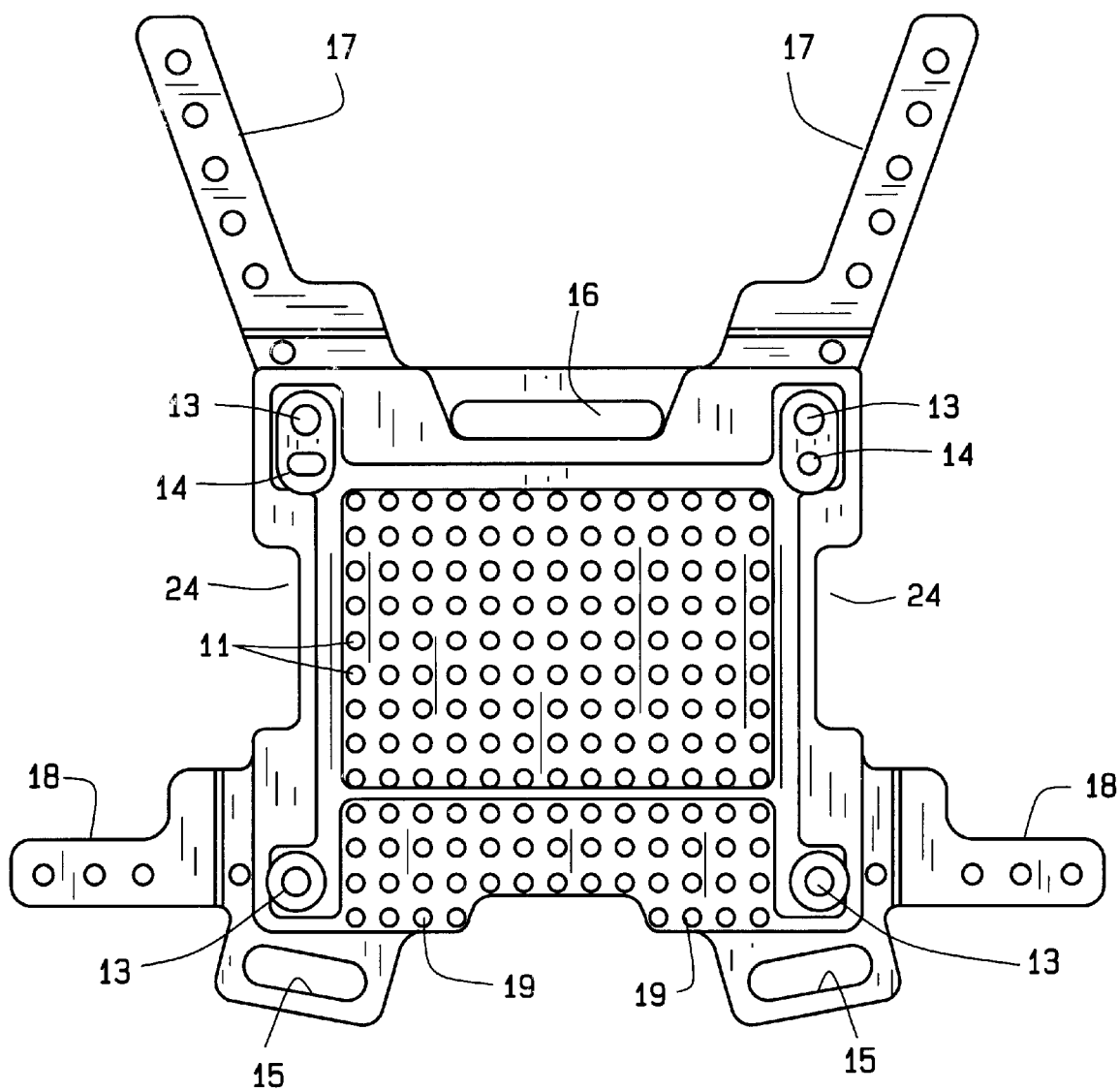
FIG. 3 is a front view of the template.

The template 1, which can also be seen in FIG. 3, is fabricated as a multishaped component, but generally, the essence of its structure is to furnish a series of precisely indexed and aligned apertures, as at 11, therethrough, and through which the seeding needle(s) locates, during performance of a seeding procedure. The series of apertures provide a grid work of needle holes, designed to accommodate this type of precision during treatment.

The template which may be fabricated of a polymer, or related materials, also includes a metal insert or frame, as at 12, which is provided for adding stability and rigidity to the template, and also furnishes precise alignment of the various apertures, as at 13, after which the various thumb screws 8 insert during fastening. In addition, the holes 14 are also provided therein for accommodating the guide pins 10, for precise alignment, when the disposable template is mounted to its frame 2.

Figure 4:
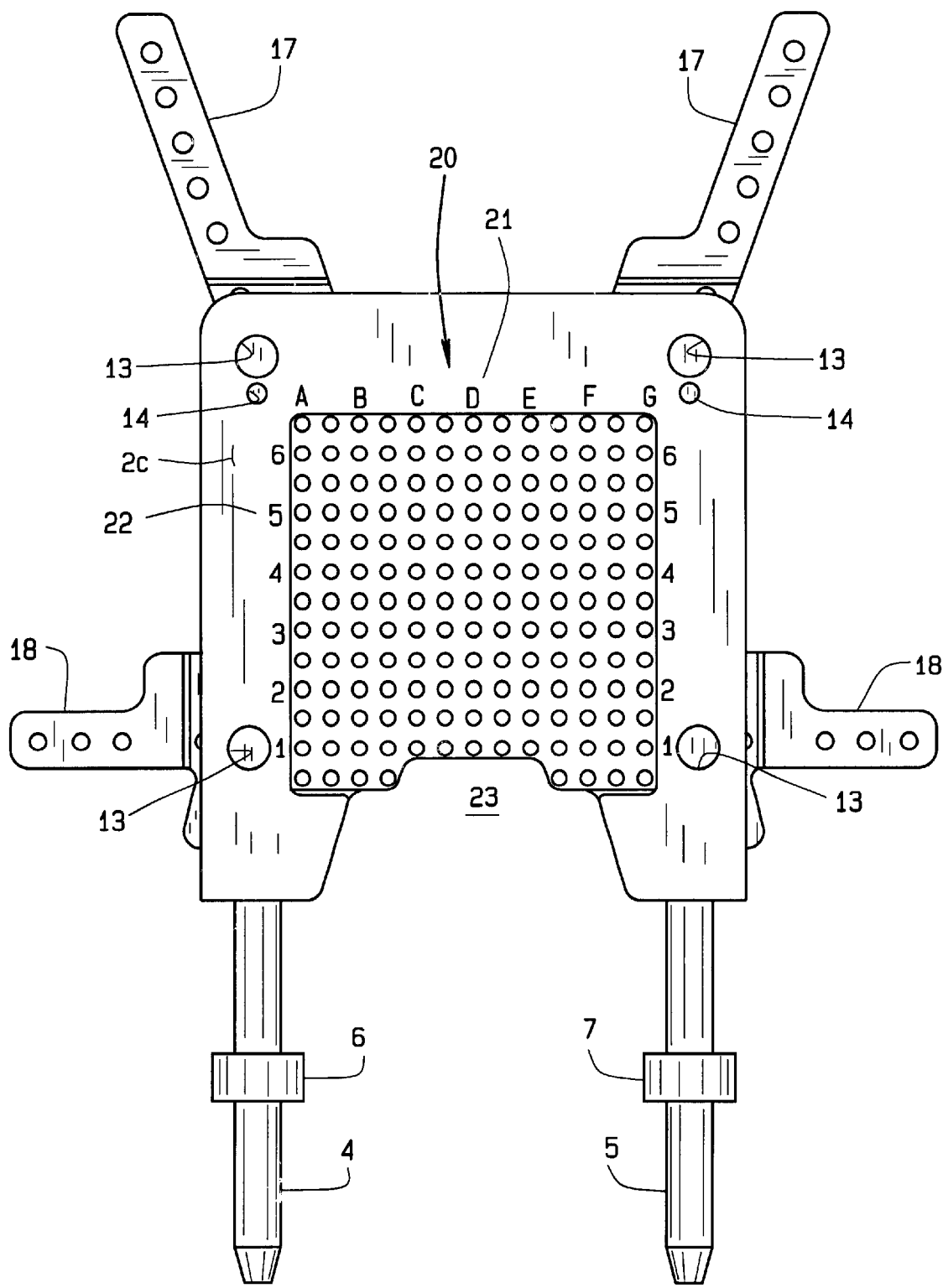
FIG. 4 is a back view of the seeding template, within the mounting frame, and disclosing the indexing indicia used during seed implantation.

Further provided upon the template are other instrumentations to facilitate the usage of the seeding device including belt loops 15, in addition to a belt loop 16, all of which are to accommodate a belt, to allow for this template to be secured to the patient, where it is necessary to remove the template, with its emplaced needles, in the prostate, to separate it from the instrument but yet maintain the template in proximity with the patient, during and subsequent to treatment. Furthermore, suture wings 17 extend upwardly from the template. Further lateral suture wings 18, are also provided for facilitating usage of this device by the technician, the nurses, and the treating physician, when suturing the template to the patient. Some of the lower disposed needle holes, as at 19, are furnished for accommodating the surgical vesicles. The back view of the disposable template 1, as mounted within the frame 2, as shown in FIG. 4. This also provides the disclosure of the indicia, as at 20, on the back surface of the mounting frame back 2c, such as the lettering provided at 21 along the abscissa, and the numerical indexing as at 22, providing for the blank coordinates, for precise locating of the aperture for needle insertion during treatment of the prostate. The mounting frame wall 2d cradles the template 1, so that the apertures 11 and 19 of the template align with the indicia 21 and 22 for precise placement of the needles. As can also be noted from the device of FIG. 4, there is an open design, as at 23, furnishing clearance, so that the interface will clear the flexible devices inserted into the template upon removal from the implanting device.

Figure 5:
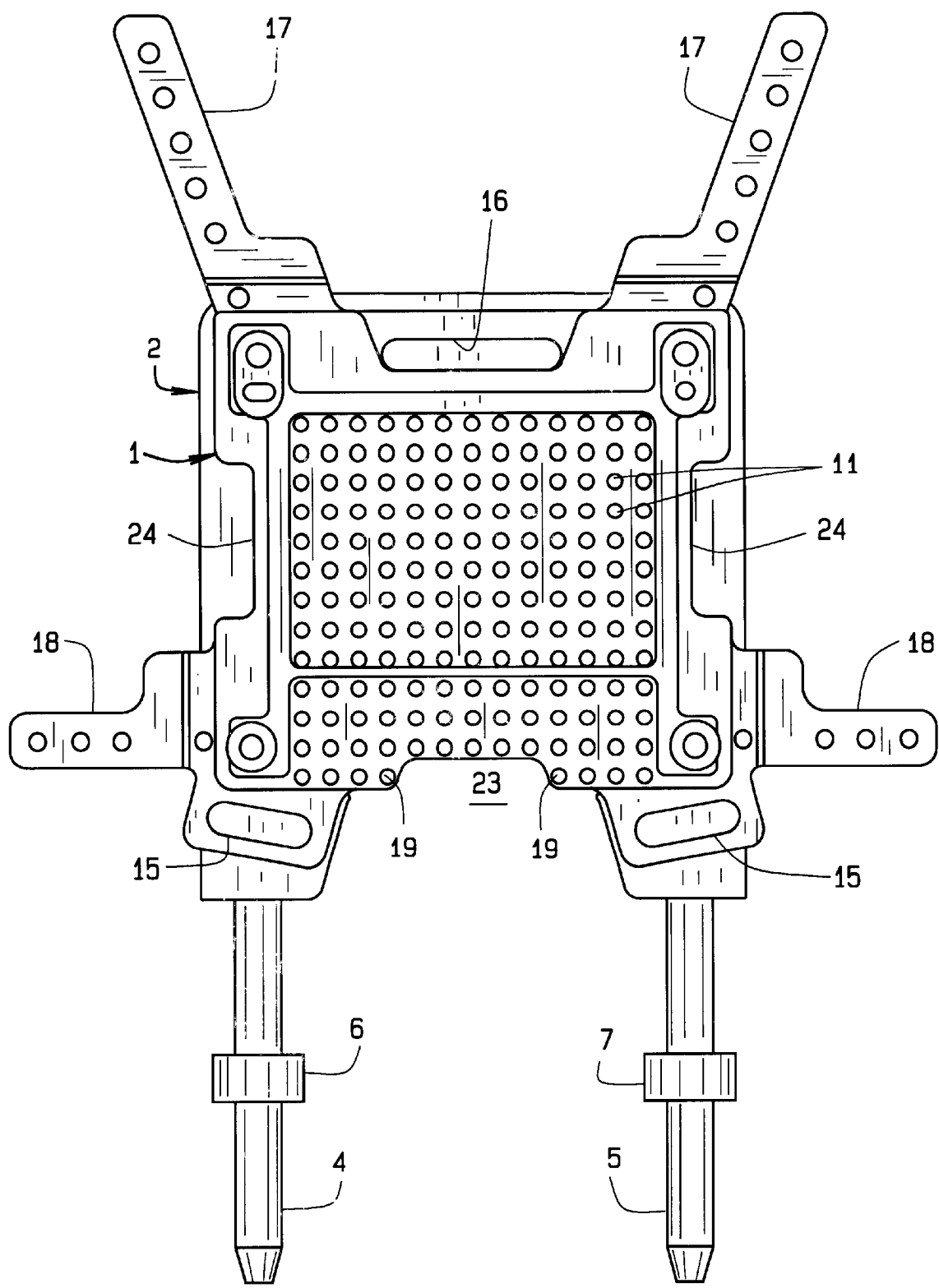
FIG. 5 is a back view of the disposable template and its mounting frame.

FIG. 5 provides a front view of the disposable template 1, secured within its mounting frame 2, as can be noted. As can also be seen, the sleeves 6 and 7 are actually positioning sleeves, that can be fixed, by means of set screws or Allen screws, at various positions along the length of the vertical grid posts 4 and 5, to provide for precision in the arrangement of the approximate height of the template 1, during its initial assembly and installation upon its heating device.

Also provided, as can be noted from FIG. 5, is the arrangement of finger grips, as at 24, upon either side of the template 1, and which furnishes clearance for interface registration features of the device, during usage.

Figure 6:
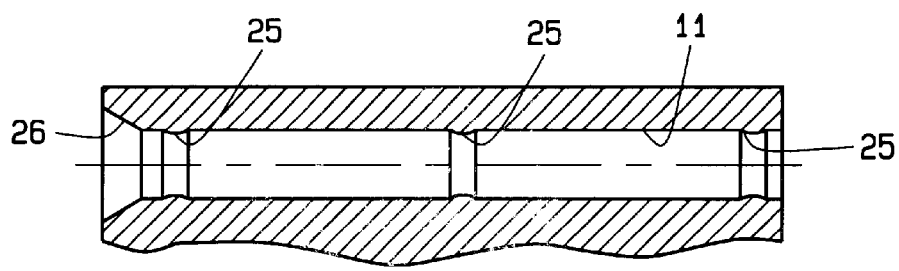
FIG. 6 provides a cross-sectional view of the template taken through one of the needle insertion apertures of the template.

FIG. 6 shows a cross-section of each of the apertures 11 furnished through the template, and as can be noted, these apertures 11 include a main bore that provides alignment for the needle along a desired path, it includes a series of detents, as at 25, that helps control the insertion, and removal force of the needle, once installed. Three detents 25 are shown, near the front of the aperture 11, one near the back of the aperture 11, and one in the approximate center of the aperture 11. The template apertures 11 could include fewer or more detents, as may be desired. In addition, the front end of the aperture 11 includes a flared portion, as at 26, to facilitate the initial insertion of the needle through the template during usage. Obviously, as can be understood, there may be a plurality of such seeding needles that are installed through the template, and into the prostate, to provide complete treatment.

In use, the template 1 can be used freehand or docked to a stepper/stabilizer. When used freehand, the template 1 the mounting frame 2 is note used. Rather, the suture wings 17 and 18 and belt loops 15 and 16 are used to anchor, or secure, the template in place relative to the patient. When used freehand, the template 1 provides guiding and anchoring means for interventional devices associated with brachytherapy seed implants, high dose rate brachytherapy, cryotherapy, and RF therapy, such as needles and catheters. When docked to the stepper/stabilizer, the mounting frame 2 serves as an interface to secure the template 1 to the stepper/stabilizer 3 and maintain the template in register with the calibration tank or stabilization device. Additionally, as noted above, the use of the thumbscrews 8, enable the template to be easily dismounted from the mounting frame 2 (and hence from the stepper/stabilizer) to allow the template to remain with the patient, such as may be required during high dose brachytherapy procedures. Further, the open space 23 below the template and hence defined by the frame legs 2a and the bottom of the template defines a clearance which will clear flexible devices (such as a high dose brachytherapy afterloader) inserted into the upon removal of the template 1 from the stepper/stabilizer 3. The mounting frame 2, via the thumbscrews 8, allows for the template to be reconnected to the stepper/stabilizer, regardless of what interventional devices are connected to the template, and for whatever reason. The pins 10 will help properly align the template 1 with the indicia 20 when the template is reconnected to the stepper/stabilizer.

Variations or modifications to the subject matter of this invention may occur to those skilled in the art upon reviewing the subject matter of this invention as provided herein. Such variations, if within the spirit of this development, are intended to be encompassed within the scope of the invention as disclosed. The description of the preferred embodiment, as generally illustrate in the drawings, is provided for illustration purposes only.

What is claimed is:

1. A prostate treatment apparatus comprising, in combination, a prostate treatment template and a separate mounting frame; said template being mountable to said frame, and said mounting frame being mountable to a seed implant device;

said template comprising:

a template body having a plurality of apertures extending therethrough;

fasteners for removably securing said template to said mounting frame;

suture wings extending from said template body to facilitate suturing of said template to a patient; and belt loops sized to receive a belt to secure the template to a patient.

2. The combination of claim 1 wherein said template body include a rigid body frame and a polymer portion molded to said body frame.

3. The combination of claim 2 wherein said template body includes openings through which said fasteners extend; said openings being positioned in said body frame.

4. The combination of claim 1 wherein said apertures include at least one area of reduced diameter.

5. The combination of claim 4 wherein said at least one area of reduced diameter in said apertures includes a detent in said aperture.

6. The combination of claim 3 wherein said mounting frame includes pins extending from said mounting frame; said template including openings through pins pass when said template is mounted to said mounting frame to properly align said template on said frame.

7. A prostate treatment template comprising a body having a rigid body frame and a polymer portion molded to said body frame; a plurality of guidance apertures extending through said body; said body frame including at least a pair of spaced apart legs and cross-member extending between and connecting said legs; said legs and cross-member defining a center area; said apertures being positioned in said center area.

8. The prostrate treatment template of claim 7 including at least one detent in each of said guidance apertures.

9. The prostrate treatment template of claim 8 including a flare opening to said guidance apertures.

10. The prostate treatment template of claim 7 including suture wings extending from said body to facilitate suturing said template to a patient during use.

11. The prostate treatment template of claim 7 including belt loops sized to accommodate a support belt to facilitate securing the template to a patient during use.

12. The prostate treatment template of claim 7 including finger grips to facilitate hand manipulation of said template.

* * * * *